United States Patent [19]

Weinstock

[11] 4,069,824
[45] Jan. 24, 1978

[54] METHOD OF AND APPARATUS FOR FORMING A CRESCENTIC JOINT IN A BONE

[76] Inventor: Robert E. Weinstock, 19230 Mack, Grosse Pointe Farms, Mich. 48236

[21] Appl. No.: 704,451

[22] Filed: July 12, 1976

[51] Int. Cl.² ............................................. A61B 17/14
[52] U.S. Cl. ...................................... 128/317; 408/54; 408/204
[58] Field of Search ....................... 30/113.1; 128/317; 408/54, 204, 207

[56] References Cited

U.S. PATENT DOCUMENTS

| 1,150,279 | 8/1915 | Little | 408/204 X |
|---|---|---|---|
| 2,557,364 | 6/1951 | Treace | 128/317 |
| 2,573,462 | 10/1951 | Lindsay | 408/204 X |
| 3,130,763 | 4/1964 | Schlosser et al. | 408/205 |
| 3,610,768 | 10/1971 | Cochran | 408/204 |

Primary Examiner—Channing L. Pace
Attorney, Agent, or Firm—Krass & Young

[57] ABSTRACT

As part of the process of realigning the distal ends of a bone having an intermediate section of width W, an arcuate osteotomy is performed on the intermediate section using a cutter having an arcuate cutting edge of a diameter slightly greater than W and an arcuate extent of 180°−N°. The blade is oscillated through an arc of approximately N° to form a crescentic joint having a maximum bearing area.

8 Claims, 4 Drawing Figures

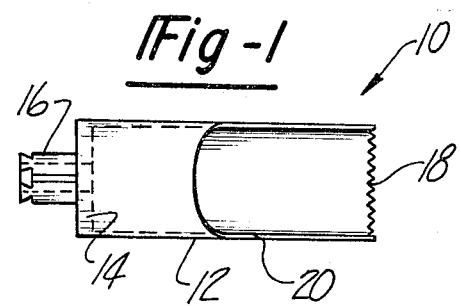
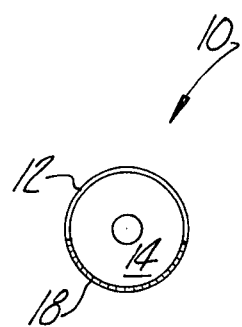
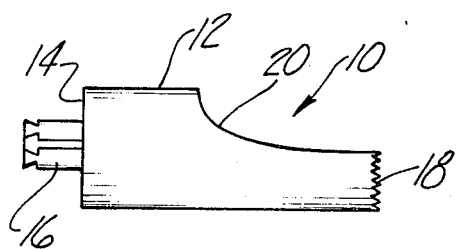
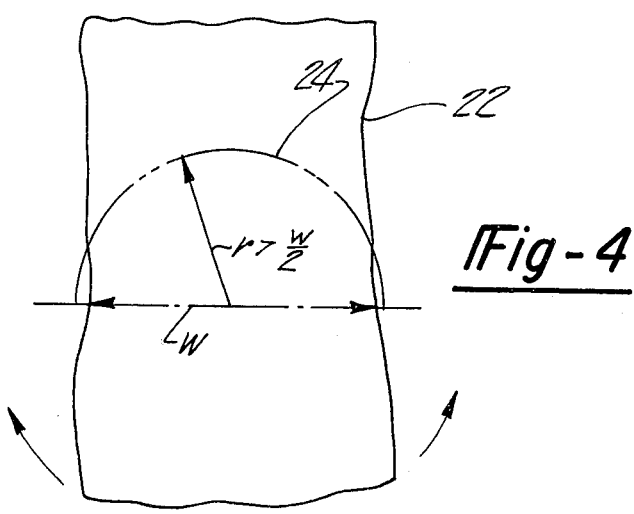

METHOD OF AND APPARATUS FOR FORMING A CRESCENTIC JOINT IN A BONE

BACKGROUND OF THE INVENTION

1. Field of the Invention

This invention relates to a method of forming a crescentic bearing joint in a bone section and to a saw and blade adapted to perform that method.

2. Prior Art

In order to realign distal ends of bone structures it has previously been proposed that an arcuate or crescent shaped cut be made through an intermediate section of the bone to effectively form a crescentic bearing joint section, and that the two ends be rotated about the joint to the desired angle and set in this new relationship.

These arcuate osteotomies were first performed by creating multiple displaced parallel drill holes which were then joined or connected using a small osteotome. It was then proposed to form the arcuate cut through the use of a bone scoop as an attachment for a rotary oscillating saw. See *Hallux Valgus Technique Using Crescentic Osteotomies* by Dr. Fritz A. Moeller collected in *The Evaluation and Treatment of Basic Foot Deformities*, Intercontinental Medical Book Corp., New York, 1974. These scoops have thin edges backed by a driving section of increased thickness and the joints formed by these scoops would tend to be non-uniform in depth, creating difficulties when the bone sections were realigned.

Osteotomes have also been developed which employ thin, arcuate blades of uniform cross-section. These blades have a serrated edge and have a driving end adapted to be supported in an oscillating saw. The blades typically have an arcuate extension of approximately 20° and 30° and the entire length of the blade has this same arcuate extension. This design creates several problems when used to perform an arcuate osteotomy. First, it is difficult to form a cut having a substantially larger arcuate extent than the arcuate extent of the blade end without forming an excessively thick cut wherein a substantial volume of bone is destroyed. Accordingly, using these blades of 20° to 30° in arcuate extent, it is not good practice to make cuts of more than about 40° to 45° in extent. As a result the relatively shallow joints thus formed were susceptible to substantial misalignment. Also, the blades had a tendency to flex out of shape if they were formed in lengths required to make cuts of substantial depth.

SUMMARY OF THE INVENTION

The present invention is directed toward a method of forming cylindrical bearing joints in bones and to an arcuate saw blade for the practice of the method which obviates the disadvantages of the prior art devices. Broadly, the present invention involves use of blades having arcuate ends which extend through the major portion of a semi-circle, i.e., less than 180° and greater than about 170°. These blades are formed of tubular stainless steel of a uniform thickness. One side of the tube is cut away, beginning a short distance from the driving end of the blade. The cut-away section fairs between the fully tubular end and the semi-circular cutting end. The cutting end has a longitudinal extension of uniform arcuate cross-section so the fairing extends along an intermediate section between the fully tubular driving end and the arcuate cutting end. This structure effectively reinforces the cutting end against flexure and provides blades that are stiff despite their substantial length.

The blades of the present invention are driven by rotationally oscillatory saws that oscillate the blades through an arc equal to 180° minus the arcuate extent of the saw's cutting edge; that is, if the saw has an arcuate extent of 173°, the saw will have an oscillatory arc of approximately 7°.

Accordingly, at any instant, a major portion of the bone cut being made is contacted by the saw blade and therefore the blade closely tracks the groove it forms in the bone, producing a sharp, well-defined cut.

The method of the present invention involves employing a blade having a diameter slightly greater than the width of the bone section at which the joint is to be formed. If the bone section has a width of ½ inch, the saw will have a slightly greater diameter, say 9/16 of an inch. Accordingly, the blade will form almost a full 180° cut in the bone and the two sections of the joint will have a maximum bearing area relative to one another, insuring an accurate realignment of the distal sections.

The combination of the use of a blade having a diameter slightly greater than the width of the section to be cut; the provision of a blade having almost a full semi-circular arcuate extension; and the rigidity provided by the blades's unique design, insures that the joints formed by the present invention will be sharply defined and close fitting, promoting quick setting of the realigned joint.

Other objectives, advantages and applications of the present invention will be made apparent by the following detailed description of the preferred embodiment of the method and apparatus of the present invention.

The description makes reference to the accompanying drawings in which:

FIG. 1 is a top view of a blade representing a preferred embodiment of the apparatus of the present invention;

FIG. 2 is a side view of the blade of FIG. 1;

FIG. 3 is an end view of the blade of FIG. 1; and

FIG. 4 is a diagram illustrating the dimensions of the blade of the present invention, relative to a bone section being cut.

Referring to the drawings, a cutter blade 10, representing a preferred embodiment of the apparatus of the present invention, is preferably formed of stainless steel. The blade has a tubular body 12 closed at one end by a transverse wall 14. A longitudinally extending shank 16 has one end fixed to the wall 14 so as to project away from the wall in a direction opposite to the body section 12. The shank 16 may be either cylindrical or triangular in cross-section and is adapted to fit in the chuck or collet of a rotational oscillatory saw. The saw may be of any commercially available type, such as a Model 1620 Standard Oscillating Bone Saw manufactured by Stryker Corporation, Kalamazoo, Mich.

The saw used with the cutter 10 preferably oscillates the cutter blade through an arc substantially equal to the difference between 180° and the arcuate extension of the cutting edge 18. Thus, the cutter makes a 180° cut in a bone section.

The diameter of the tubular section 12 of the blade 10 will depend upon the width of the bone section being cut, and will be very slightly greater than the width of that section. A typical cutter may have a diameter of ⅜ of an inch with a wall thickness of approximately 0.0325 inches.

The section 12 is fully tubular for about 40% of the length of the section, beginning at the wall 14, and the extreme cutting end 18 has an arcuate extension of slightly less than 180°, typically about between 170° and 175°. Between these two extremes, the tubular section is cut away with a concave fairing cut 20. The cut is such that the section adjacent to the cutting end 18 has an arcuate extension of somewhat less than 180° for some length back from the cutting edge 18 toward the wall 14.

The cutting edge 18 is serrated in a conventional manner to provide a suitable cutting surface.

FIG. 4 illustrates the relationship between a bone section 22 and a cut 24 made by a blade of the present invention. At the cut, the bone section has a width W. The cutter chosen has a diameter slightly greater than W/2. Accordingly, the cut made in the bone will have an arcuate extent of slightly less than 180°. This is the maximum bearing area obtainable for a the joint. It is seen that the cut 24 extends for the major portion of 180° in separating the bone section into two parts. It provides a maximum bearing area and creates conditions for minimum setting time for the bone.

The embodiments of the invention in which an exclusive property or privilege is claimed are defined as follows:

1. A saw adapted to form a crescentic joint in a bone at a section having a width W, comprising: a blade having a circular base section of a diameter slightly greater than W, an arcuate cutting end of the same diameter, the end having a serrated edge forming an arc of approximately 180°−N° formed on a circular semi-tubular section having the same arc, the other end of the semi-tubular section being connected to an intermediate tubular section that fairs out in arcuate extent from a full circle at the base to the semi-tubular section; a bit affixed centrally to the base and projecting therefrom axially in a direction opposite to the cutting end; and a rotationally oscillating drive adapted to receive the bit and oscillate through an arc of substantially N°, whereby the saw is adapted to form a crescentic osteotomy having a bearing surface of approximately 180°.

2. The saw of claim 1 which the blade has a substantially uniform thickness from its tubular base to its arcuate cutting end.

3. The saw of claim 1 wherein the intermediate tubular section connecting the end to the base has an arcuate extent of 180°−N° over a longitudinally extending section adjacent the end and a full circular section over a longitudinal extending section adjacent to the base.

4. The saw of claim 1 wherein N is less than 10°.

5. A saw blade adapted to be used with a rotationally oscillating drive which oscillates through an arc of substantially N°, to form a crescentic joint in a bone at a section having a width W, comprising: a circular base section of a diameter slightly greater than W; an arcuate cutting end of the same diameter, the end having a serrated edge forming an arc of approximately 180°−N° and being formed on a circular semi-tubular section of appreciable longitudinal extent and of the same arc; and an intermediate tubular section connecting the semi-tubular section and to the base that fairs in arcuate extent from a full circle at the base; and a shank affixed centrally to the base and projecting therefrom axially in a direction oppoite to the cutting end.

6. The blade of claim 5 wherein the tubular section of the blade, including the intermediate section and the cutting edge, has a substantially uniform thickness along its entire length.

7. The blade of claim 5 where N is less than 10°.

8. The method of performing an arcuate osteotomy in a bone section having a width W, comprising: sawing the bone section with a right, circular, cylindrical tubular blade having a diameter slightly greater than W and an arcuate cutting end formed on the same diameter and having an arcuate extent of substantially 180°−N°, by rotationally oscillating the blade through an arc of N°.

* * * * *